United States Patent
Superak et al.

(10) Patent No.: US 6,916,974 B2
(45) Date of Patent: Jul. 12, 2005

(54) INBRED SQUASH LINE 833

(75) Inventors: Ted Superak, Davis, CA (US); Donna Weiland, Dixon, CA (US)

(73) Assignee: Harris Moran Seed Company, Modesto, CA (US)

( * ) Notice: Subject to any disclaimer, the term of this patent is extended or adjusted under 35 U.S.C. 154(b) by 0 days.

(21) Appl. No.: 10/082,707

(22) Filed: Feb. 25, 2002

(65) Prior Publication Data

US 2003/0163853 A1 Aug. 28, 2003

(51) Int. Cl.⁷ .............. A10H 1/00; A10H 5/00; A10H 5/10; C12N 15/82
(52) U.S. Cl. ............. 800/310; 800/260; 800/303; 800/298; 800/300; 800/301; 800/302; 800/279; 800/278; 435/410
(58) Field of Search ................ 800/260, 310, 800/298, 300, 301, 302, 303, 279, 278; 435/410

(56) References Cited

U.S. PATENT DOCUMENTS 5,959,184 A * 9/1999 Superak ............... 800/310
6,031,158 A * 2/2000 Miller et al. ............ 800/310

OTHER PUBLICATIONS

Kraft et al, 2000, Theor. Appl. Genet. 101:323–326.*

* cited by examiner

*Primary Examiner*—Anne Kubelik
(74) *Attorney, Agent, or Firm*—Jondle & Associates, P.C.

(57) ABSTRACT

An inbred squash line, designated 833, is disclosed. The invention relates to the seeds of inbred squash line 833, to the plants of inbred squash line 833 and to methods for producing a squash plant, either inbred or hybrid, by crossing the inbred line 833 with itself or another squash line. The invention further relates to methods for producing a squash plant containing in its genetic material one or more transgenes and to the transgenic plants produced by that method and to methods for producing other inbred squash lines derived from the inbred 833.

21 Claims, No Drawings

INBRED SQUASH LINE 833

BACKGROUND OF THE INVENTION

The present invention relates to a new and distinctive squash inbred line, designated inbred 833. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, field performance, fruit and agronomic quality such as smoothness, moist texture, color, shape and size, flesh color or texture, resistance to diseases and insects, tolerance to drought and heat, plant habit and size, easier harvest ability, less need for fertilizers.

Practically speaking, all cultivated forms of squash belong to genus Cucurbita that is grown for its edible fruit. As a crop, squash, whether summer or winter squash, are grown commercially wherever environmental conditions permit the production of an economically viable yield. Both are harvested by hand. Squash usually develop a running vine on the soil but today's summer squash have been developed in the form of a short compact bush, making them easier to grow in smaller spaces. On healthy winter squash plants, there is a canopy of large, reniform and serrated leaves, which may be without lobes or with very deep ones. Fruit flesh can be of various shade of yellow, or even from white to orange. The fruits may have a soft or a hard shell with colors from dull to bright. Summer squash show a great variety of shape, cylindrical, long, flat, etc., with sizes from small to large and colors from uniform to variegated. The flesh can range from white to yellow and, contrary to the winter squash that has a flesh finely grained, bear coarse grains. In the United States, the principal fresh market squash growing regions are California, Florida and Georgia which produce approximately 30,000 acres out of a total annual acreage of more than 57,000 acres (USDA, 2000). Fresh squash are available in the United States year-round although the greatest supply is from June through October. Summer squash are consumed immature as table vegetables and winter squash are used when ripe as table vegetable or in pie.

*Cucurbita pepo* is a member of the family Cucurbitaceae. The Cucurbitaceae is a family of about 90 genera and 700 to 760 species, mostly of the tropics. The family includes pumpkins, squash, gourds, watermelon, loofah and several weeds. The genus *cucurbita*, to which the squash belongs, includes four major species, *pepo, argyrosperma, moschata*, and *maxima*, one minor species, *ficifolia* and some wild ones. Cross-pollination is near complete among the different *cucurbita* species. This offers breeders a great potential for inter-specific crosses using conventional breeding procedures. *Cucurbita pepo* L. refers to what is commonly known as the summer squash such as scallop, zucchini, straightneck and crookneck types and winter squash such as acorn and pumpkin. The term squash itself has a rather large meaning. Generally, it can be said that if the plant produce fruits to be harvested in an immature stage, they are called summer squash, and if the fruits are to be harvested at maturity, they are called winter squash.

Squash is a simple diploid species with twelve pairs of highly differentiated chromosomes. The plants are monoecious, with separate female and male flowers on the same plant. Usually the first four or five flowers produced are male, then the next eight or so are female, followed by a few more male and female flowers. Male flowers have 3–5 erect stamens bunched within the corolla of 5 fused petals. Female flowers have 3 spreading stigma lobes and an immature fruit (ovary) below the perianth. The spiny, sticky pollen requires insects for pollination. The primary pollinators are bees, particularly honey bees. Pollination generally occurs in the morning after the flowers open.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for three years at least. The best lines are candidates for new commercial cultivars; those still deficient in a few traits are used as parents to produce new populations for further selection.

These processes, which lead to the final step of marketing and distribution, usually take from eight to 12 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior squash inbred lines and hybrids. The breeder initially selects and crosses two or more parental lines, followed by repeated selfing and selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same squash traits.

Each year, the plant breeder selects the germplasm to advance to the next generation. This germplasm is grown under unique and different geographical, climatic and soil conditions, and further selections are then made, during and at the end of the growing season. The inbred lines which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same line twice by using the exact same original parents and the same selection techniques. This unpredictability results in the expenditure of large research monies to develop a superior new squash inbred line.

The development of commercial squash hybrids requires the development of homozygous inbred lines, the crossing of these lines, and the evaluation of the crosses. Pedigree breeding and recurrent selection breeding methods are used to develop inbred lines from breeding populations. Breeding programs combine desirable traits from two or more inbred lines or various broad-based sources into breeding pools from which inbred lines are developed by selfing and selection of desired phenotypes. The new inbreds are crossed with other inbred lines and the hybrids from these crosses are evaluated to determine which have commercial potential.

Pedigree breeding is used commonly for the improvement of self-pollinating crops or inbred lines of cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., "Principles of Plant Breeding" John Wiley and Son, pp. 115–161, 1960; Allard, 1960; Simmonds, 1979; Sneep et al., 1979; Fehr, 1987).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Once the inbreds that give the best hybrid performance have been identified, the hybrid seed can be reproduced indefinitely as long as the homogeneity of the inbred parent is maintained. A single-cross hybrid is produced when two inbred lines are crossed to produce the $F_1$ progeny.

Squash is an important and valuable field crop. Thus, a continuing goal of plant breeders is to develop stable, high yielding squash hybrids that are agronomically sound. The reasons for this goal are obviously to maximize the amount of fruit produced on the land used as well as to improve the fruit agronomic qualities. To accomplish this goal, the squash breeder must select and develop squash plants that have the traits that result in superior parental lines for producing hybrids.

SUMMARY OF THE INVENTION

According to the invention, there is provided a novel inbred squash line, designated inbred 833. This invention thus relates to the seeds of inbred squash line 833, to the plants of inbred squash line 833 and to methods for producing a squash plant produced by crossing the inbred line 833 with itself or another squash line, and to methods for producing a squash plant containing in its genetic material one or more transgenes and to the transgenic squash plants produced by that method. This invention also relates to methods for producing other inbred squash lines derived from inbred squash line 833 and to the inbred squash lines derived by the use of those methods. This invention further relates to hybrid squash seeds and plants produced by crossing the inbred line 833 with another squash line.

In another aspect, the present invention provides regenerable cells for use in tissue culture of inbred squash plant 833. The tissue culture will preferably be capable of regenerating plants having the physiological and morphological characteristics of the foregoing inbred squash plant, and of regenerating plants having substantially the same genotype as the foregoing inbred squash plant. Preferably, the regenerable cells in such tissue cultures will be embryos, protoplasts, meristematic cells, callus, pollen, leaves, anthers, stems, petioles, roots, root tips, fruits, seeds, flowers or the like. Still further, the present invention provides squash plants regenerated from the tissue cultures of the invention.

Another objective of the invention is to provide methods for producing other inbred squash plants derived from inbred squash line 833. Inbred squash lines derived by the use of those methods are also part of the invention.

The invention also relates to methods for producing a squash plant containing in its genetic material one or more transgenes and to the transgenic squash plant produced by that method.

In another aspect, the present invention provides for single gene converted plants of inbred 833. The single transferred gene may preferably be a dominant or recessive allele. Preferably, the single transferred gene will confer such trait as herbicide resistance, insect resistance, resistance for bacterial, fungal, or viral disease, improved harvest characteristics, enhanced nutritional quality. The single gene may be a naturally occurring squash gene or a transgene introduced through genetic engineering techniques.

The invention further provides methods for developing squash plant in a squash plant breeding program using plant breeding technique including recurrent selection, backcrossing, pedigree breeding, restriction fragment length polymorphism enhanced selection, genetic marker enhanced selection and transformation. Seeds, squash plant, and parties thereof produced by such breeding methods are also part of the invention.

DEFINITIONS

In the description and tables that follow, a number of terms are used. In order to provide a clear and consistent understanding of the specification and claims, including the scope to be given such terms, the following definitions are provided:

Adaptability. A plant that has adaptability is a plant able to grow well in different growing conditions (climate, soils, etc.).

Allele. The allele is any of one or more alternative form of a gene, all of which alleles relates to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Earliness. Earliness of a plant is a relative definition of when the plant starts to bear fruits in regard to other plants that will bear fruits later.

Easy to pick fruit. A fruit that is easy to pick is a fruit that easily detaches from the plant. Once grabbed and twisted, the fruit will break between the peduncle and the stem. For fruits not easy to pick, the peduncle breaks off the fruits.

Essentially all the physiological and morphological characteristics. A plant having essentially all the physiological and morphological characteristics means a plant having the physiological and morphological characteristics, except for the characteristics derived from the converted gene.

Extended harvest. An extended harvest is a plant that produces fruits throughout the harvest season.

Good Seed Producer. A plant is a good seed producer when it produces numerous seeds. For squash, a good seed producing plant will produce an average of 25 grams of seeds during the harvest season.

Mid-Season. The mid-season plant is a plant that is harvested approximately 50 days after planting. An early plant would have 45 days from planting to harvest while a late one will have 55 days.

Open Plant Habit. An open plant habit is a plant where the fruits are visible without moving the leaves. A plant with closed habit will have its fruit hidden by leaves that have a high density. An average open plant habit will be between the open and closed habit, and the plant will have medium leaf density.

Plant Habit. A plant can be an upright plant (also called erect) or can be sprawling on the ground. It can also be pendant.

Quantitative Trait Loci (QTL) Quantitative trait loci refer to genetic loci that control to some degree numerically representable traits that are usually continuously distributed.

Regeneration. Regeneration refers to the development of a plant from tissue culture.

Ribs. The ribs on the fruit may be prominent, inconspicuous or nonexistent. They refer to the ridges along the fruit mostly near the peduncle.

Single gene converted. Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Small plant. A small plant has short internodes with petiole lengths of approximately 40 cm and a plant height of 40 to 60 cm. It depends on how the plant spreads out horizontally or vertically.

Large plant. A large plant has long internodes with a plant height of 75 cm and above. It depends on how the plant spreads out horizontally or vertically.

Vigor. The vigor of a plant is a rating of the amount of vegetative growth after emergence at the seedling stage.

DETAILED DESCRIPTION OF THE INVENTION

Inbred squash line 833 is a mid-season gray zucchini summer squash with superior characteristics, and provides an excellent parental line in crosses for producing first generation ($F_1$) hybrid squash. Inbred squash line 833 is particularly suitable to produce gray zucchini hybrids best adapted to the Middle East and Mexico area, however, its superior characteristics and resistances make it usable to produce a wide range of varieties in many other areas such as North America and European Countries, especially Italy, France and Spain. Inbred squash line 833 is an excellent seed producer. At marketable maturity, it bears gray, short blocky tapered fruit having a rounded base, a smooth surface with inconspicuous ribs. The yield is very high, with an extended harvest. The inbred is a small plant having a large type plant growth with an open plant habit. The color of the vine is a very dark green. Inbred squash line 833 is resistant to Zucchini Yellow Mosaic Virus (ZYMV) and Powdery Mildew (PM) and tolerant to Watermelon Mosaic Virus (WMV) and Papaya Ringspot Virus (PRSV). Inbred 833 will be used to produce mid-season high yielding hybrids, with plants having an open habit, with easy to pick fruits having a color from grey in Mexico to pale for Middle East and having resistance to Zucchini Yellow Mosaic Virus and Powdery Mildew and tolerance to Watermelon Mosaic Virus and Papaya Ringspot Virus.

Inbred line 833 has superior characteristics and was developed from the cross of plots 1499×1500 made in the spring of 1992 in Florida. The F1 plants were grown in a Zucchini Yellow Mosaic Virus workshop in the Spring of 1993 in Florida and self pollinated. Pedigree selection for good plant type, fruit type, and resistance to Zucchini Yellow Mosaic Virus and powdery mildew was used on successive generations in the Fall, 1993, Spring, 1994, Fall, 1994, and Spring 1995 seasons in Florida. Two additional selfs were made successively in the Summers of 1996 and 1997 in Davis, Calif. In 1998 the first cage increase was made in Davis. Selection pressure was first for resistance to Zucchini Yellow Mosaic virus and Powdery Mildew, but also for earliness, for an open plant having female characteristics (numerous female flowers). Color and shape of the fruit as well as ease of pick of the fruits from the plant were also sought when the inbred was developed.

Inbred 833 is similar to the cultivar 'Zucchini Grey'. 'Zucchini Grey' is also a summer type squash. While similar to inbred 833, 'Zucchini Grey' has numerous differences including: 'Zucchini Grey' is a plant having a closed habit while 833 has an open one, inbred 833 is a mid-season inbred while 'Zucchini Grey' is a late season and furthermore inbred 833 is resistant to Zucchini Yellow Mosaic Virus (ZYMV) and Powdery Mildew (PM) while 'Zucchini Grey' is not.

Zucchini Yellow Mosaic Virus and Powdery Mildew resistances are traits that are especially desired for a squash variety. The ZYMV virus incites yellow mosaic, blisters as well as necrosis and plant stunning. The fruits may develop deformation and the seed production may be severely reduced. The ZYMV is a potyvirus spread by different aphid species, and is extremely difficult to control by insecticides. Powdery Mildew is another threat to squash production. It reduces the size and number of fruits, thus decreasing the yields. *Sphaerotheca fuliginea* and *Erysiphe cichoracearum* are the two most common powdery mildew pathogens. Their action creates whitish, talcum like powdery fungal growth on leaf surfaces, on petioles as well as on leaves. Therefore, ZYMV and Powdery Mildew resistant squash may be of great value in new squash varieties development. During the development of the line, crosses were made to inbred testers for the purpose of estimating the line's general and specific combining ability, and parallel evaluations were run in the USA by the Davis, Calif. Research Station. The inbred was evaluated further as a line and in numerous crosses by Davis, Calif. Research station. The inbred has proven to have a good combining ability in hybrid combinations.

The inbred line has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in inbred 833.

Inbred squash line 833 has the following morphologic and other characteristics (based primarily on data collected at Davis, Calif.).

VARIETY DESCRIPTION INFORMATION

SPECIES: pepo
KIND: squash
TYPE: summer
COTYLEDONS:
Length: 65.8 mm
Width 33 mm
Apex: rounded
Veining: Obscure
Color: medium green
PLANT
Bush, prickly
LEAVES:
Shape: reniform
Shape: deeply lobed
medium green
blotched with grey
Margin: dentate
Width: 34.6 cm
Long: 32.2 cm
Dorsal Surface: bristled
Ventral Surface: bristled
Petiole lenght: 40 cm
FLOWER—Pistillate
Flower: 9 cm diameter
Ovary: drum like
Pedicel: 3 cm length
Margin: straight
Margin: plain
Sepals: 2 mm width
Sepals: 13 mm length
Color: deep yellow
FLOWER—Staminate
Sepals: 2 mm width
Sepals: 20 mm length
Pedicel: 14 cm length
Color: deep yellow
FRUIT (at market maturity):
Length: 11 cm
Stem end: 4.5 cm width
Blossom end: 4.8 cm width
Apex: flattened
Base: rounded
Ribs: inconspicuous
Rib furrows: none
Fruit surface: smooth
Warts: none
Blossom scar button: slightly extended
RIND:
Thickness at medial: 2 mm
Rind: tough
Color pattern: lace, regular
FLESH:
Thickness: 19 mm blossom end
Thickness: 16.5 mm medial
Thickness: 29 mm stem end
Texture: firm
Texture: moist
Flavor: insipid,
Quality: good
Color: cream
SEED CAVITY:
Length: 17.5 cm
Width: 9.8 cm
Location: conform to fruit shape
Placenta tissue: moderately abundant
Center core: prominent
FRUIT STALKS:
Length: 3.95 cm
Diameter: 3 cm
slightly curved
Texture: hard
Farrows: deep
Surface: smooth
Attachment end: expanded
Detaches: with difficulty
Color: dark green
SEEDS:
Length: 15.6 mm
Width: 8.5 mm Thickness: 3.1 mm
Face surface: smooth
Color: cream
Margin: straight,
Margin: wedge-like
Separation from pulp: easy
Number of seeds per fruit: 299
Weight of 100 seeds: 14 gm
DISEASE RESISTANCE Rating (1=susceptible-2=tolerant-3=resistant)
Cucumber Mosaic: N/A
Zucchini Yellow Mosaic Virus: 3
Powdery mildew: 3
Watermelon mosaic: 2
Papaya Ringspot Virus: 2
Squash mosaic: N/A
Verticillum wilt: N/A
Downy mildew: N/A

FURTHER EMBODIMENTS OF THE INVENTION

This invention also is directed to methods for producing a squash plant by crossing a first parent squash plant with a second parent squash plant wherein either the first or second parent squash plant is an inbred squash plant of the line 833. Further, both first and second parent squash plants can come from the inbred squash line 833. Still further, this invention also is directed to methods for producing an inbred squash line 833-derived squash plant by crossing inbred squash line 833 with a second squash plant and growing the progeny seed, and repeating the crossing and growing steps with the inbred squash line 833-derived plant from 0 to 7 times. Thus, any such methods using the inbred squash line 833 are part of this invention: selfing, backcrosses, hybrid production, crosses to populations, and the like. All plants produced using inbred squash line 833 as a parent are within the scope of this invention, including plants derived from inbred squash line 833. Advantageously, the inbred squash line is used in crosses with other, different, squash inbreds to produce first generation ($F_1$) squash hybrid seeds and plants with superior characteristics.

As used herein, the term plant includes plant cells, plant protoplasts, plant cell tissue cultures from which squash plants can be regenerated, plant calli, plant clumps and plant cells that are intact in plants or parts of plants, such as embryos, pollen, ovules, flowers, leaves, stalks, and the like.

As it is well known in the art, tissue culture of squash can be used for the in vitro regeneration of squash plants. Tissues cultures of various tissues of squash and regeneration of plants therefrom are well known and published. By way of example, a tissue culture comprising organs has been used to produce regenerated plants as described in Kintzios et al., Acta Horticulturae. 1998, 461, 427–432, Chee-P P. Hort Science, 1992, 27: 1, 59–60, Chee-P P. Plant Cell Report1991, 9: 11, 620–622, Juretic et al., Plant Cell Report. 1991, 9: 11, 623–626, Rakoczy et al., Plant Cell Tissue and Organ Culture 1989, 18: 2,191–194, Hegazi H H. Arab University Journal of Agricultural Science. 1999, 7: 2, 507–520, also Schroder, Bot Gaz. 129:374–376 (1968) reported the production of embryogenic tissue from pericarp tissues of squash. Jelaska, Planta 103:278–280 (1972) and Acta Bot. Croat. 32: 81–94 (1973) reported somatic embryogenesis in hypocotyl and cotyledon-derived callus of pumpkins and demonstrated that embryos could develop into normal plants. Pink et al., Sci. Hortic. 24:107–114 (1984) reported a rapid propagation method for pumpkin through apical meristem culture. See also Toppi et al., Plant Cell Tissue and Organ Culture 51:2 89–93 (1997) and U.S. Pat. No. 5,677,157 filed in 1994. It is clear from the literature that the state of the art is such that these methods of obtaining plants are, and were, "conventional" in the sense that they are routinely used and have a very high rate of success. Thus, another aspect of this invention is to provide cells which upon growth and differentiation produce squash plants having the physiological and morphological characteristics of inbred squash line 833.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native, or endogenous, genes (perhaps driven by different promoters) in order to alter the traits of a plant in a specific manner. Such foreign additional and/or modified genes are referred to herein collectively as "transgenes". Over the last fifteen to twenty years several methods for producing transgenic plants have been developed, and the present invention, in particular embodiments, also relates to transformed versions of the claimed inbred line.

Plant transformation involves the construction of an expression vector which will function in plant cells. Such a vector comprises DNA comprising a gene under control of or operatively linked to a regulatory element (for example, a promoter). The expression vector may contain one or more such operably linked gene/regulatory element combinations. The vector(s) may be in the form of a plasmid, and can be used alone or in combination with other plasmids, to provide transformed squash plants, using transformation methods as described below to incorporate transgenes into the genetic material of the squash plant(s).

Expression Vectors for Squash Transformation

Marker Genes—Expression vectors include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation arts, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (nptII) gene, isolated from transposon Tn5, which when placed under the control of plant regulatory signals confers resistance to kanamycin. Fraley et al., Proc. Natl. Acad. Sci. U.S.A., 80:4803 (1983). Another commonly used selectable marker gene is the hygromycin phosphotransferase gene which confers resistance to the antibiotic hygromycin. Vanden Elzen et al., Plant Mol. Biol., 5:299 (1985).

Additional selectable marker genes of bacterial origin that confer resistance to antibiotics include gentamycin acetyl transferase, streptomycin phosphotransferase, aminoglycoside-3'-adenyl transferase, the bleomycin resistance determinant. Hayford et al., Plant Physiol. 86:1216 (1988), Jones et al., Mol. Gen. Genet., 210:86 (1987), Svab et al., Plant Mol. Biol. 14:197 (1990<Hille et al., Plant Mol. Biol. 7:171 (1986). Other selectable marker genes confer resistance to herbicides such as glyphosate, glufosinate or broxynil. Comai et al., *Nature* 317:741–744 (1985), Gordon-Kamm et al., *Plant Cell* 2:603–618 (1990) and Stalker et al., *Science* 242:419–423 (1988).

Other selectable marker genes for plant transformation are not of bacterial origin. These genes include, for example, mouse dihydrofolate reductase, plant 5-enolpyruvylshikimate-3-phosphate synthase and plant acetolactate synthase. Eichholtz et al., *Somatic Cell Mol. Genet.* 13:67 (1987), Shah et al., *Science* 233:478 (1986), Charest et al., *Plant Cell Rep.* 8:643 (1990).

Another class of marker genes for plant transformation require screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include beta-glucuronidase (GUS), alpha-galactosidase, luciferase and chloramphenicol, acetyltransferase. Jefferson, R. A., *Plant Mol. Biol. Rep.* 5:387 (1987), Teeri et al., *EMBO J.* 8:343 (1989), Koncz et al., *Proc. Natl. Acad. Sci U.S.A.* 84:131 (1987), DeBlock et al., *EMBO J.* 3:1681 (1984).

Recently, in vivo methods for visualizing GUS activity that do not require destruction of plant tissue have been made available. Molecular Probes publication 2908, Imagene Green™, p. 1–4 (1993) and Naleway et al., *J. Cell Biol.* 115:151a (1991). However, these in vivo methods for visualizing GUS activity have not proven useful for recovery of transformed cells because of low sensitivity, high fluorescent backgrounds and limitations associated with the use of luciferase genes as selectable markers.

More recently, a gene encoding Green Fluorescent Protein (GFP) has been utilized as a marker for gene expression in prokaryotic and eukaryotic cells. Chalfie et al., *Science* 263:802 (1994). GFP and mutants of GFP may be used as screenable markers.

Promoters—Genes included in expression vectors must be driven by nucleotide sequence comprising a regulatory element, for example, a promoter. Several types of promoters are now well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Examples of promoters under developmental control include promoters that preferentially initiate transcription in certain tissues, such as leaves, roots, seeds, fibers, xylem vessels, tracheids, or sclerenchyma. Such promoters are referred to as "tissue-perferred". Promoters which initiate transcription only in certain tissue are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters constitute the class of "non-constitutive" promoters. A "constitutive" promoter is a promoter which is active under most environmental conditions.

A. Inducible Promoters

An inducible promoter is operably linked to a gene for expression in squash. Optionally, the inducible promoter is operably linked to a nucleotide sequence encoding a signal sequence which is operably linked to a gene for expression in squash. With an inducible promoter the rate of transcription increases in response to an inducing agent.

Any inducible promoter can be used in the instant invention. See Ward et al., *Plant Mol. Biol.* 22:361–366 (1993). Exemplary inducible promoters include, but are not limited to, that from the ACEI system which responds to copper (Meft et al., *PNAS* 90:4567–4571 (1993)); In2 gene from maize which responds to benzenesulfonamide herbicide safeners (Hershey et al., *Mol. Gen Genetics* 227:229–237 (1991) and Gatz et al., *Mol. Gen. Genetics* 243:32–38 (1994)) or Tet repressor from Tn10 (Gatz et al., *Mol. Gen. Genetics* 227:229–237 (1991). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena et al., *Proc. Natl. Acad. Sci. U.S.A.* 88:0421 (1991).

B. Constitutive Promoters

A constitutive promoter is operably linked to a gene for expression in squash or the constitutive promoter is operably linked to a nucleotide sequence encoding a signal sequence which is operably linked to a gene for expression in squash.

Many different constitutive promoters can be utilized in the instant invention. Exemplary constitutive promoters include, but are not limited to, the promoters from plant viruses such as the 35S promoter from CaMV (Odell et al., *Nature* 313:810–812 (1985) and the promoters from such genes as rice actin (McElroy et al., *Plant Cell* 2:163–171 (1990)); ubiquitin (Christensen et al., *Plant Mol. Biol.* 12:619–632 (1989) and Christensen et al., *Plant Mol. Biol.* 18:675–689 (1992)); pEMU (Last et al., *Theor. Appl. Genet.* 81:581–588 (1991)); MAS (Velten et al., *EMBO J.* 3:2723–2730 (1984)) and maize H3 histone (Lepetit et al., *Mol. Gen. Genetics* 231:276–285 (1992) and Atanassova et al., *Plant Journal* 2 (3):291–300 (1992)).

The ALS promoter, Xba1/Ncol fragment 5' to the *Brassica napus* ALS3 structural gene (or a nucleotide sequence similarity to said Xba1/Ncol fragment), represents a particularly useful constitutive promoter. See PCT application WO96/30530.

C. Tissue-Specific or Tissue-Preferred Promoters

A tissue-specific promoter is operably linked to a gene for expression in squash. Optionally, the tissue-specific promoter is operably linked to a nucleotide sequence encoding a signal sequence which is operably linked to a gene for expression in squash. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., *Science* 23:476–482 (1983) and Sengupta-Gopalan et al., *Proc. Natl. Acad. Sci. U.S.A.* 82:3320–3324 (1985)); a leaf-specific and light-induced promoter such as that from cab or rubisco (Simpson et al., *EMBO J.* 4(11):2723–2729 (1985) and Timko et al., *Nature* 318:579–582 (1985)); an anther-specific promoter such as that from LAT52 (Twell et al., *Mol. Gen. Genetics* 217:240–245 (1989)); a pollen-specific promoter such as that from Zm13 (Guerrero et al., *Mol. Gen. Genetics* 244:161–168 (1993)) or a microspore-preferred promoter such as that from apg (Twell et al., *Sex. Plant Reprod.* 6:217–224 (1993).

Signal Sequences for Targeting Proteins to Subcellular Compartments

Transport of protein produced by transgenes to a subcellular compartment such as the chloroplast, vacuole, peroxisome, glyoxysome, cell wall or mitochondroin or for secretion into the apoplast, is accomplished by means of operably linking the nucleotide sequence encoding a signal sequence to the 5' and/or 3' region of a gene encoding the protein of interest. Targeting sequences at the 5' and/or 3' end of the structural gene may determine, during protein synthesis and processing, where the encoded protein is ultimately compartmentalized.

The presence of a signal sequence directs a polypeptide to either an intracellular organelle or subcellular compartment or for secretion to the apoplast. Many signal sequences are known in the art. See, for example Becker et al., *Plant Mol. Biol.* 20:49 (1992), Close, P. S., Master's Thesis, Iowa State University (1993), Knox, C., et al., "Structure and Organization of Two Divergent Alpha-Amylase Genes from Barley", *Plant Mol. Biol.* 9:3–17 (1987), Lerner et al., *Plant Physiol.* 91:124–129 (1989), Fontes et al., *Plant Cell* 3:483–496 (1991), Matsuoka et al., *Proc. Natl. Acad. Sci.* 88:834 (1991), Gould et al., *J. Cell. Biol.* 108:1657 (1989), Creissen et al., *Plant J.* 2:129 (1991), Kalderon, et al., A short amino acid sequence able to specify nuclear location, *Cell* 39:499–509 (1984), Steifel, et al., Expression of a maize cell wall hydroxyproline-rich glycoprotein gene in early leaf and root vascular differentiation, *Plant Cell* 2:785–793 (1990).

Foreign Protein Genes and Agronomic Genes

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114:92–6 (1981).

According to a preferred embodiment, the transgenic plant provided for commercial production of foreign protein is squash. In another preferred embodiment, the biomass of interest is seed. For the relatively small number of transgenic plants that show higher levels of expression, a genetic map can be generated, primarily via conventional RFLP, PCR and SSR analysis, which identifies the approximate chromosomal location of the integrated DNA molecule. For exemplary methodologies in this regard, see Glick and Thompson, Methods in Plant Molecular Biology and Biotechnology CRC Press, Boca Raton 269:284 (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, agronomic genes can be expressed in transformed plants. More particularly, plants can be genetically engineered to express various phenotypes of agronomic interest. Exemplary genes implicated in this regard include, but are not limited to, those categorized below:

1. Genes that Confer Resistance to Pests or Disease and that Encode:

A. Plant disease resistance genes. Plant defenses are often activated by specific interaction between the product of a disease resistance gene (R) in the plant and the product of a corresponding avirulence (Avr) gene in the pathogen. A plant inbred line can be transformed with cloned resistance gene to engineer plants that are resistant to specific pathogen strains. See, for example Jones et al., *Science* 266:789 (1994) (cloning of the tomato Cf-9 gene for resistance to *Cladosporium fulvum*); Martin et al., *Science* 262:1432 (1993) (tomato Pto gene for resistance to *Pseudomonas syringae* pv. Tomato encodes a protein kinase); Mindrinos et al., *Cell* 78:1089 (1994) (Arabidopsis RSP2 gene for resistance to *Pseudomonas syringae*).

B. A *Bacillus thuringiensis* protein, a derivative thereof or a synthetic polypeptide modeled thereon. See, for example, Geiser et al., *Gene* 48:109 (1986), who disclose the cloning and nucleotide sequence of a Bt ä-endotoxin gene. Moreover, DNA molecules encoding a-endotoxin genes can be purchased from American Type Culture Collection, Manassas, Va., for example, under ATCC Accession Nos. 40098, 67136, 31995 and 31998.

C. Genes coding for both capsid proteins of the Squash Mosaic Comovirus (SqMV), see Pang et al., *Molecular Breeding*. 2000, 6: 1, 87–93, which once expressed in the plant allows it to be resistant to the SqMV D. A lectin. See, for example, the disclose by Van Damme et al., *Plant Molec. Biol.* 24:25 (1994), who disclose the nucleotide sequences of several *Clivia miniata* mannose-binding lectin genes.

E. An enzyme inhibitor, for example, a protease or proteinase inhibitor or an amylase inhibitor. See, for example, Abe et al., *J. Biol. Chem.* 262:16793 (1987) (nucleotide sequence of rice cysteine proteinase inhibitor), Huub et al., *Plant Molec. Biol.* 21:985 (1993) (nucleotide sequence of cDNA encoding tobacco proteinase inhibitor I), Sumitani et al., *Biosci. Biotech. Biochem.* 57:1243 (1993) (nucleotide sequence of *Streptomyces nitrosporeus* á-amylase inhibitor).

F. An insect-specific hormone or pheromone such as an ecdysteroid and juvenile hormone, a variant thereof, a mimetic based thereon, or an antagonist or agonist thereof. See, for example, the disclosure by Hammock et al., *Nature* 344:458 (1990), of baculovirus expression of cloned juvenile hormone esterase, an inactivator of juvenile hormone.

G. An insect-specific peptide or neuropeptide which, upon expression, disrupts the physiology of the affected pest. For example, see the disclosures of Regan, *J. Biol. Chem.* 269:9 (1994) (expression cloning yields DNA coding for insect diuretic hormone receptor), and Pratt et al., *Biochem. Biophys. Res. Comm.* 163:1243 (1989) (an allostatin is identified in Diploptera puntata). See also U.S. Pat. No. 5,266,317 to Tomalski et al., who disclose genes encoding insect-specific, paralytic neurotoxins.

H. An insect-specific venom produced in nature by a snake, a wasp, etc. For example, see Pang et al., *Gene* 116:165 (1992), for disclosure of heterologous expression in plants of a gene coding for a scorpion insectotoxic peptide.

I. An enzyme responsible for a hyper accumulation of a monterpene, a sesquiterpene, a steroid, hydroxamic acid, a phenylpropanoid derivative or another non-protein molecule with insecticidal activity.

J. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., Insect Biochem. Molec. Biol. 23:691 (1993), who teach the nucleotide sequence of a cDNA encoding tobacco hookworm chitinase, and Kawalleck et al., Plant Molec. Biol. 21:673 (1993), who provide the nucleotide sequence of the parsley ubi4-2 polyubiquitin gene.

K. A molecule that stimulates signal transduction. For example, see the disclosure by Botella et al., Plant Molec. Biol. 24:757 (1994), of nucleotide sequences for mung bean calmodulin cDNA clones, and Griess et al., Plant Physiol. 104:1467 (1994), who provide the nucleotide sequence of a maize calmodulin cDNA clone.

L. A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance), the respective contents of which are hereby incorporated by reference.

M. A membrane permease, a channel former or a channel blocker. For example, see the disclosure of Jaynes et al., Plant Sci 89:43 (1993), of heterologous expression of a cecropin-â, lytic peptide analog to render transgenic tobacco plants resistant to Pseudomonas solanacearum.

N. A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., Ann. rev. Phytopathol. 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

O. An insect-specific antibody or an immunotoxin derived therefrom. Thus, an antibody targeted to a critical metabolic function in the insect gut would inactivate an affected enzyme, killing the insect. Cf. Taylor et al., Abstract #497, Seventh Int'l Symposium on Molecular Plant-Microbe Interactions (Edinburgh, Scotland) (1994) (enzymatic inactivation in transgenic tobacco via production of single-chain antibody fragments).

P. A virus-specific antibody. See, for example, Tavladoraki et al., Nature 366:469 (1993), who show that transgenic plants expressing recombinant antibody genes are protected from virus attack.

Q. A developmental-arrestive protein produced in nature by a pathogen or a parasite. Thus, fungal endo á-1, 4-D-polygalacturonases facilitate fungal colonization and plant nutrient release by solubilizing plant cell wall homo-á-1,4-D-galacturonase. See Lamb et al., Bio/Technology 10:1436 (1992). The cloning and characterization of a gene which encodes a bean endopolygalacturonase-inhibiting protein is described by Toubart et al., Plant J. 2:367 (1992).

R. A development-arrestive protein produced in nature by a plant. For example, Logemann et al., Bioi/Technology 10:305 (1992), have shown that transgenic plants expressing the barley ribosome-inactivating gene have an increased resistance to fungal disease.

S. A combination of Zucchini Yellow Mosaic Potyvirus and Watermelon Mosaic 2 Potyvirus coat proteins expressed by transgenic cucurbita lines and allowing such lines not to develop severe foliar symptoms. See Fuchs et al., BioTechnology. 1995, 13: 13, 1466–1473.

2. Genes that Confer Resistance to a Herbicide, For Example:

A. A herbicide that inhibits the growing point or meristem, such as an imidazalinone or a sulfonylurea. Exemplary genes in this category code for mutant ALS and AHAS enzyme as described, for example, by Lee et al., EMBO J. 7:1241 (1988), and Miki et al., Theor. Appl. Genet 80:449 (1990), respectively.

B. Glyphosate (resistance impaired by mutant 5-enolpyruvl-3-phosphikimate synthase (EPSP) and aroA genes, respectively) and other phosphono compounds such as glufosinate (phosphinothricin acetyl transferase, PAT and Streptomyces hygroscopicus phosphinothricin-acetyl transferase, bar, genes), and pyridinoxy or phenoxy propionic acids and cycloshexones (ACCase inhibitor-encoding genes). See, for example, U.S. Pat. No. 4,940,835 to Shah, et al., which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061 to Comai. European patent application No. 0 333 033 to Kumada et al., and U.S. Pat. No. 4,975,374 to Goodman et al., disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al., DeGreef et al., Bio/Technology 7:61 (1989), describe the production of transgenic plants that express chimeric bar genes coding for phosphinothricin acetyl transferase activity. Exemplary of genes conferring resistance to phenoxy propionic acids and cycloshexones, such as sethoxydim and haloxyfop are the Acc1-S1, Acc1-S2 and Acc1-S3 genes described by Marshall et al., Theor. Appl. Genet. 83:435 (1992).

C. A herbicide that inhibits photosynthesis, such as a triazine (psbA and gs+ genes) and a benzonitrile (nitrilase gene). Przibilla et al., Plant Cell 3:169 (1991), describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al., Biochem. J. 285:173 (1992).

3. Genes that Confer or Contribute to a Value-Added Trait, Such as:

A. Modified fatty acid metabolism, for example, by transforming a plant with an antisense gene of stearyl-ACP desaturase to increase stearic acid content of the plant. See Knultzon et al., Proc. Natl. Acad. Sci. U.S.A. 89:2624 (1992).

B. Decreased phytate content

1) Introduction of a phytase-encoding gene would enhance breakdown of phytate, adding more free phosphate to the transformed plant. For example, see Van Hartingsveldt et al., Gene 127:87 (1993), for a disclosure of the nucleotide sequence of an Aspergillus niger phytase gene.

2) A gene could be introduced that reduced phytate content. In maize, this, for example, could be accomplished, by cloning and then reintroducing DNA associated with the single allele which is responsible for maize mutants characterized by low levels of phytic acid. See Raboy et al., *Maydica* 35:383 (1990).

C. Modified carbohydrate composition effected, for example, by transforming plants with a gene coding for an enzyme that alters the branching pattern of starch. See Shiroza et al., *J. Bacteol.* 170:810 (1988) (nucleotide sequence of *Streptococcus mutants* fructosyltransferase gene), Steinmetz et al., *Mol. Gen. Genet.* 20:220 (1985) (nucleotide sequence of *Bacillus subtilis* levansucrase gene), Pen et al., *Bio/Technology* 10:292 (1992) (production of transgenic plants that express *Bacillus licheniformis* á-amylase), Elliot et al., *Plant Molec. Biol.* 21:515 (1993) (nucleotide sequences of tomato invertase genes), Søgaard et al., *J. Biol. Chem.* 268:22480 (1993) (site-directed mutagenesis of barley á-amylase gene), and Fisher et al., *Plant Physiol.* 102:1045 (1993) (maize endosperm starch branching enzyme II).

Methods for Squash Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick B. R. and Thompson, J. E. Eds. (CRC Press, Inc., Boca Raton, 1993) pages 67–88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick B. R. and Thompson, J. E. Eds. (CRC Press, Inc., Boca Raton, 1993) pages 89–119.

A. Agrobacterium-Mediated Transformation

One method for introducing an expression vector into plants is based on the natural transformation system of Agrobacterium. See, for example, Toppi et al., *Plant Cell Tissue and Organ Culture*. 1997, 51: 2, 89–93, Katavic et al., *Plant Cell Tissue and Organ Culture*. 1991, 24: 1, 35–42, Valles et al., *PI Cell. Rep.* 145–148:13 (1984). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant Sci.* 10:1 (1991). Descriptions of Agrobacterium vector systems and methods for Agrobacterium-mediated gene transfer are provided by Gruber et al., supra, Miki et al., supra, and Moloney et al., *Plant Cell Reports* 8:238 (1989). See also, U.S. Pat. No. 6.198.022 issued Mar. 6, 2001.

B. Direct Gene Transfer

Despite the fact the host range for Agrobacterium-mediated transformation is broad, some major cereal crop or vegetable species and gymnosperms have generally been recalcitrant to this mode of gene transfer, even though some success has recently been achieved in rice and corn. Hiei et al., *The Plant Journal* 6:271–282 (1994) and U.S. Pat. No. 5,591,616 issued Jan. 7, 1997. Several methods of plant transformation, collectively referred to as direct gene transfer, have been developed as an alternative to Agrobacterium-mediated transformation.

A generally applicable method of plant transformation is microprojectile-mediated transformation wherein DNA is carried on the surface of microprojectiles measuring 1 to 4 im. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5:27 (1987), Sanford, J. C., *Trends Biotech.* 6:299 (1988), Klein et al., *Bio/Technology* 6:559–563 (1988), Sanford, J. C., *Physiol Plant* 7:206 (1990), Klein et al., *Biotechnology* 10:268 (1992).

Another method for physical delivery of DNA to plants is sonication of target cells. Zhang et al., *Bio/Technology* 9:996 (1991). Alternatively, liposome or spheroplast fusion have been used to introduce expression vectors into plants. Deshayes et al., *EMBO J.*, 4:2731 (1985), Christou et al., *Proc Natl. Acad. Sci. U.S.A.* 84:3962 (1987). Direct uptake of DNA into protoplasts using $CaCl_2$ precipitation, polyvinyl alcohol or poly-L-omithine have also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4:1495–1505 (1992) and Spencer et al., *Plant Mol. Biol.* 24:51–61 (1994).

Following transformation of squash target tissues, expression of the above-described selectable marker genes allows for preferential selection of transformed cells, tissues and/or plants, using regeneration and selection methods now well known in the art.

The foregoing methods for transformation would typically be used for producing a transgenic inbred line. The transgenic inbred line could then be crossed, with another (non-transformed or transformed) inbred line, in order to produce a new transgenic inbred line. Alternatively, a genetic trait which has been engineered into a particular squash line using the foregoing transformation techniques could be moved into another line using traditional backcrossing techniques that are well known in the plant breeding arts. For example, a backcrossing approach could be used to move an engineered trait from a public, non-elite inbred line into an elite inbred line, or from an inbred line containing a foreign gene in its genome into an inbred line or lines which do not contain that gene. As used herein, "crossing" can refer to a simple X by Y cross, or the process of backcrossing, depending on the context.

When the term inbred squash plant is used in the context of the present invention, this also includes any single gene conversions of that inbred. The term single gene converted plant as used herein refers to those squash plants which are developed by a plant breeding technique called backcrossing wherein essentially all of the desired morphological and physiological characteristics of an inbred are recovered in addition to the single gene transferred into the inbred via the backcrossing technique. Backcrossing methods can be used with the present invention to improve or introduce a characteristic into the inbred. The term backcrossing as used herein refers to the repeated crossing of a hybrid progeny back to one of the parental squash plants for that inbred. The parental squash plant which contributes the gene for the desired characteristic is termed the nonrecurrent or donor parent. This terminology refers to the fact that the nonrecurrent parent is used one time in the backcross protocol and therefore does not recur. The parental squash plant to which the gene or genes from the nonrecurrent parent are transferred is known as the recurrent parent as it is used for several rounds in the backcrossing protocol (Poehiman & Sleper, 1994; Fehr, 1987). In a typical backcross protocol, the original inbred of interest (recurrent parent) is crossed to a second inbred (nonrecurrent parent) that carries the single gene of interest to be transferred. The resulting progeny from this cross are then crossed again to the recurrent parent and the process is repeated until a squash plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original inbred. To accomplish this, a single gene of the recurrent inbred is modified or substituted with the desired gene from the nonrecurrent parent, while retaining essentially all of the rest of the desired genetic, and therefore the desired physiological and morphological, constitution of the original inbred. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new inbred but that can be improved by backcrossing techniques. Single gene traits may or may not be transgenic, examples of these traits include but are not limited to, herbicide resistance (such as bar or pat genes), resistance for bacterial, fungal, or viral disease (capsid protein genes), insect resistance, enhanced nutritional quality, yield stability and yield enhancement. These genes are generally inherited through the nucleus. Some known exceptions to this are the genes for male sterility, some of which are inherited cytoplasmically, but still act as single gene traits. Several of these single gene traits are described in U.S. Pat. Nos. 5,777,196; 5,948,957 and 5,969,212, the disclosures of which are specifically hereby incorporated by reference.

Tables

In the tables that follow, the traits and characteristics of hybrid containing inbred squash 833 as a parent are given compared to other hybrids. The data collected are presented for key characteristics and traits. Inbred 833 was tested in several hybrid combinations at numerous locations, with two or three replications per location. Information about these hybrids, as compared to several check hybrids is presented Table 1, 2 and 3: Hybrid characteristics of the plant The hybrid formula/hybrid name is shown in column 1. Goya and Anita are hybrid checks and SSXP776, SSXP823 and 833*8324 are hybrids having 833 as a parent.

The vigor of the plant is shown in column 2 with a rating from 1 to 9, 1 being very weak, 9 being very strong.

The health of the plant is shown in column 3 with a rating from 1 to 9, 1 being very susceptible, 9 being very strong.

The adaptability of the plant is shown in column 4 with a rating from 1 to 9, 1 being not adaptable, 9 being very adaptable.

The earliness of the plant is shown in column 5 with a rating from 1 to 9, 1 being very late, 9 being very early.

The habit of the plant is shown in column 6 with a rating from 1 to 9, 1 being very pendant, 9 being very erect.

The density of the plant is shown in column 7 with a rating from 1 to 9, 1 being very dense, 9 being very open.

TABLE 1

Overall Comparisons
Hybrids with 833 as a parent vs. Check Hybrids
Location: Jordan 2000 Date: Mar. 20, 2000

| Inbred | Vigor | Health | Adaptability | Earliness | Habit | Density |
|---|---|---|---|---|---|---|
| Anita (check) | 7 | 7 | 8 | 7 | 7 | 6 |
| Goya (check) | 4 | 5 | 4 | 9 | 8 | 7 |
| SSXP776 | 7 | 8 | 7 | 8 | 7 | 6 |
| 833*8324 | 7 | 6 | 7 | 8 | 7 | 7 |
| SSXP823 | 7 | 6 | 6 | 6 | 8 | 7 |

TABLE 2

Overall Comparisons
Hybrids with 833 as a parent vs. Check Hybrids
Location: Jordan 2000 Date: Mar. 26, 2000

| Inbred | Vigor | Health | Adaptability | Earliness | Habit | Density |
|---|---|---|---|---|---|---|
| Anita (check) | 7 | 8 | 8 | | 7 | 6 |
| Goya (check) | 5 | 6 | 7 | | 7 | 7 |
| SSXP776 | 6 | 6 | 7 | | 7 | 6 |
| 833*8324 | 7 | 7 | 7 | | 8 | 7 |
| SSXP823 | 8 | 7 | 7 | | 8 | 6 |

TABLE 3

Overall Comparisons
Hybrids with 833 as a parent vs. Check Hybrids
Location: Jordan 2000 Date: Apr. 4, 2000

| Inbred | Vigor | Health | Adaptability | Earliness | Habit | Density |
|---|---|---|---|---|---|---|
| Anita (check) | 8 | 8 | 8 | 4 | 7 | 6 |
| Goya (check) | 6 | 7 | 7 | 4 | 6 | 6 |
| SSXP776 | 6 | 6 | 7 | 4 | 8 | 7 |
| 833*8324 | 7 | 6 | 6 | 5 | 8 | 8 |
| SSXP823 | 7 | 7 | 5 | 8 | 4 | 6 |

Table 4, 5 and 6: Hybrid characteristics of the fruit

The hybrid formula/hybrid name is shown in column 1. Goya and Anita are hybrid checks and SSXP776, SSXP823 and 833*8324 are hybrids having 833 as a parent.

The uniformity of the fruit is shown in column 2 with a rating from 1 to 9, 1 being misshapen, 9 being very uniform.

The length of the fruit in centimeters is shown in column 3.

The diameter of the fruit in centimeters is shown in column 4.

The ease to harvest of the fruit is shown in column 5 with a rating from 1 to 9, 1 being very difficult, 9 being very easy.

The blossom scar of the fruit is shown in column 6 with a rating from 1 to 9, 1 being very big, 9 being very small.

TABLE 4

Overall Comparisons
Hybrids with 833 as a parent vs. Check Hybrids
Location: Jordan 2000 Date: Mar. 26, 2000

| Inbred | Uniformity | Length | Diameter | Ease to harvest | Blossom scar |
|---|---|---|---|---|---|
| Anita (check) | 7 | 8 | 3.5 | 8 | 4 |
| Goya (check) | 5 | 10 | 4 | 7 | 5 |

TABLE 4-continued

Overall Comparisons
Hybrids with 833 as a parent vs. Check Hybrids
Location: Jordan 2000 Date: Mar. 26, 2000

| Inbred | Uniformity | Length | Diameter | Ease to harvest | Blossom scar |
|---|---|---|---|---|---|
| SSXP776 | 8 | 7 | 3 | 7 | 6 |
| 833*8324 | 8 | 7 | 4.5 | 7 | 6 |
| SSXP823 | 7 | 11 | 4 | 7 | 4 |

TABLE 5

Overall Comparisons
Hybrids with 833 as a parent vs. Check Hybrids
Location: Jordan 2000 Date: Apr. 4, 2000

| Inbred | Uniformity | Length | Diameter | Ease to harvest | Blossom scar |
|---|---|---|---|---|---|
| Anita (check) | 8 | 9 | 4 | 7 | 4 |
| Goya (check) | 4 | 9 | 3.5 | 7 | 4 |
| SSXP776 | 4 | 7 | 4 | 7 | 4 |
| 833*8324 | 8 | 5 | 4 | 8 | 4 |
| SSXP823 | 7 | 8 | 4 | 6 | 4 |

TABLE 6

Overall Comparisons
Hybrids with 833 as a parent vs. Check Hybrids
Location: Jordan 2000 Date: Apr. 9, 2000

| Inbred | Uniformity | Length | Diameter | Ease to harvest | Blossom scar |
|---|---|---|---|---|---|
| Anita (check) | 8 | 10 | 4 | 8 | 4 |
| Goya (check) | 6 | 10 | 4 | 6 | 3 |
| SSXP776 | 7 | 8 | 4 | 7 | 4 |
| 833*8324 | 7 | 10 | 4.5 | 5 | 3 |
| SSXP823 | 4 | 8 | 4.5 | 4 | 5 |

Deposit Information

Deposits of the Harris Moran Seed Company proprietary inbred squash line 833 and the hybrid 833*8324 disclosed above and recited in the appended claims have been made with National Collections of Industrial Food and Marine Bacteria (NCIMB), 23 St. Machar Drive, Aberdeen, Scotland, AB24 3RY, United Kingdom. The date of deposit was Oct. 15, 2004. The deposits of 2,500 seeds each were taken from the same deposits maintained by Harris Moran Seed Company since prior to the filing date of this application. All restrictions upon the deposits have been removed, and the deposits are intended to meet all of the requirements of 37 C.F.R. §1.801-1.809. The NCIMB accession number for inbred squash line 833 is NCIMB 41250. The NCIMB accession number for hybrid 833*8324 is NCIMB 41251. The deposits will be maintained in the depository for a period of 30 years, or 5 years after the last request, or for the effective life of the patent, whichever is longer, and will be replaced as necessary during that period.

Although the foregoing invention has been described in some detail by way of illustration and example for purposes of clarity and understanding. However, it will be obvious that certain changes and modifications such as single gene modifications and mutations, somaclonal variants, variant individuals selected from large populations of the plants of the instant inbred and the like may be practiced within the scope of the invention, as limited only by the scope of the appended claims.

What is claimed is:

1. An inbred squash seed designated 833, wherein a sample of said seed has been deposited under NCIMB No. 41250.

2. A squash plant, or a part thereof, produced by growing the seed of claim 1.

3. Pollen of the plant of claim 2.

4. An ovule of the plant of claim 2.

5. A squash plant, or a part thereof, having all of the physiological and morphological characteristics of the squash plant of claim 2.

6. A tissue culture of regenerable cells of a squash plant of inbred 833, wherein the cells produce a plant having all the morphological and physiological characteristics of inbred squash line 833, and wherein a sample of representative seeds has been deposited under NCIMB No. 41250.

7. The tissue culture of claim 6, wherein the regenerable cells are from meristems, leaves, pollen, embryos, roots, root tips, flowers, anthers, stems, petioles, fruits, cotyledons or hypocotyls.

8. A squash plant regenerated from the tissue culture of claim 6, wherein the plant has all the morphological and physiological characteristics of inbred squash line 833, representative seeds having been deposited under NCIMB No. 41250.

9. A method for producing a hybrid squash seed wherein the method comprises crossing a first inbred parent squash plant with a second inbred parent squash plant and harvesting the resultant hybrid squash seed, wherein said first or second parent squash plant is the squash plant of claim 2.

10. A method of producing a transgenic squash plant wherein the method comprises transforming the squash plant of claim 2 with a transgene wherein the transgene confers a characteristic selected from the group consisting of herbicide resistance, insect resistance, resistance to bacterial disease, resistance to fungal disease, resistance to viral disease, and male sterility.

11. A transgenic squash plant produced by the method of claim 10.

12. A method of producing an herbicide resistant squash plant wherein the method comprises transforming the squash plant of claim 2 with a transgene that confers herbicide resistance.

13. An herbicide resistant squash plant produced by the method of claim 12.

14. A method of producing an insect resistant squash plant wherein the method comprises transforming the squash plant of claim 2 with a transgene that confers insect resistance.

15. An insect resistant squash plant produced by the method of claim 14.

16. A method of producing a disease resistant squash plant wherein the method comprises transforming the squash plant of claim 2 with a transgene that confers resistance to bacterial, fungal or viral disease.

17. A disease resistant squash plant produced by the method of claim 16.

18. A method of producing a male sterile squash plant wherein the method comprises transforming the squash plant of claim 2 with a transgene that confers male sterility.

19. A male sterile squash plant produced by the method of claim 18.

20. A hybrid squash seed designated 833*8324 having inbred line 833 as a parental line, representative seed of said hybrid having been deposited under NCIMB No. 41251.

21. A hybrid squash plant produced by growing the hybrid seed of claim 20.

* * * * *